US012806439B2

(12) United States Patent
Shen et al.

(10) Patent No.: US 12,806,439 B2
(45) Date of Patent: Nov. 24, 2026

(54) SYSTEM AND METHOD FOR SIMULTANEOUSLY PERFORMING PHOTODYNAMIC THERAPY AND PHOTOACOUSTIC MEASUREMENT

(71) Applicant: FENG CHIA UNIVERSITY, Taichung City (TW)

(72) Inventors: Tsu-Wang Shen, Taichung City (TW); Yi-Ru Li, Taichung City (TW)

(73) Assignee: FENG CHIA UNIVERSITY, Taichung City (TW)

( * ) Notice: Subject to any disclaimer, the term of this patent is extended or adjusted under 35 U.S.C. 154(b) by 284 days.

(21) Appl. No.: 18/633,742

(22) Filed: Apr. 12, 2024

(65) Prior Publication Data

US 2025/0073493 A1 Mar. 6, 2025

Related U.S. Application Data

(60) Provisional application No. 63/579,580, filed on Aug. 30, 2023.

(30) Foreign Application Priority Data

Jan. 19, 2024 (TW) ................................ 113102266

(51) Int. Cl.

*A61N 5/06* (2006.01)
*A61B 5/00* (2006.01)
*A61N 5/067* (2006.01)

(52) U.S. Cl.

CPC ............ *A61N 5/062* (2013.01); *A61B 5/0095* (2013.01); *A61N 5/067* (2021.08);

(Continued)

(58) Field of Classification Search

None

See application file for complete search history.

(56) References Cited

U.S. PATENT DOCUMENTS

2008/0221647 A1* 9/2008 Chamberland ........ A61N 5/062 382/131
2017/0055838 A1 3/2017 Ham (Continued)

FOREIGN PATENT DOCUMENTS

CN 1846645 A 10/2006
CN 112755405 A 5/2021

OTHER PUBLICATIONS

Office Action dated Apr. 16, 2024 of the corresponding Taiwan patent application No. 113102266.

*Primary Examiner* — Michael W Kahelin

(74) *Attorney, Agent, or Firm* — MUNCY, GEISSLER, OLDS & LOWE, P.C.

(57) ABSTRACT

A system for simultaneously performing photodynamic therapy and photoacoustic measurement includes a pulsed light source configured to emit a pulsed light; a light splitter, disposed on an optical path of the pulsed light, and configured to split the pulsed light into a first split light and a second split light; a reflector, disposed on an optical path of the first split light, and configured to reflect the first split light into a reflected light; a first lens, disposed on an optical path of the reflected light, and configured to refract the reflected light to an irradiated surface to form a first light spot; and a second lens, disposed on an optical path of the second split light, and configured to refract the second split light to the irradiated surface to form a second light spot.

14 Claims, 5 Drawing Sheets

(52) U.S. Cl.
CPC ................. *A61N 2005/0626* (2013.01); *A61N 2005/0659* (2013.01); *A61N 2005/0663* (2013.01); *A61N 2005/0665* (2013.01)

(56) References Cited

U.S. PATENT DOCUMENTS

| | | | | |
|---|---|---|---|---|
| 2018/0303349 | A1* | 10/2018 | Wang | A61B 5/0095 |
| 2019/0170695 | A1* | 6/2019 | Xiang | G01N 29/2418 |
| 2021/0369348 | A1* | 12/2021 | Cook | A61B 18/26 |

* cited by examiner

SYSTEM AND METHOD FOR SIMULTANEOUSLY PERFORMING PHOTODYNAMIC THERAPY AND PHOTOACOUSTIC MEASUREMENT

CROSS-REFERENCE TO RELATED APPLICATION

This patent application claims the benefit of U.S. Provisional Patent Application No. 63/579,580, filed Aug. 30, 2023, which is incorporated by reference herein.

BACKGROUND OF THE DISCLOSURE

Technical Field

The present disclosure relates to a system and method for simultaneously performing photodynamic therapy and photoacoustic measurement used for treatment and medical testing.

Description of Related Art

Photodynamic therapy is a biomedical technology that combines optics with biochemistry to eliminate cancer cells. Photodynamic therapy is mainly the interaction between light, photosensitizer, and oxygen. A carrier is used to target the photosensitizer to the tumor tissue. When the laser irradiates the target area of the tumor tissue, the photosensitizer absorbed by the tumor is excited, resulting in a photochemical reaction that produces reactive oxygen species to damage the cells and blood vessels in the tumor tissue. As a result, tumor growth is reduced or cancer cells are killed. Since the photodynamic reaction occurs only in the area stimulated by the laser, the treatment process does not affect normal tissues. Photodynamic therapy is a highly localized treatment technology.

Photoacoustic measurement is a biomedical imaging technology that uses the photoacoustic effect. Photoacoustic measurements usually use pulsed lasers as the excitation light source. When a short-pulse laser irradiates target tissue, the irradiated tissue absorbs energy, resulting in thermal expansion and contraction, causing high-frequency vibration to generate ultrasound. An ultrasonic transducer is used to receive the photoacoustic signals. A photoacoustic image is formed by analyzing the information contained in the photoacoustic signals.

The related-art of photodynamic therapy and photoacoustic measurement are processes that may not be performed at the same time due to factors such as energy setting, pulsed light control, and interference. Therefore, the current processes of treatment, measurement, and diagnosis need to be separated. As a result, doctors may not immediately monitor whether the tumor is cleared and make adjustments according to the treatment situation. This also results in an extended waiting time for patients throughout the process, resulting in a greater risk of illness.

In view of this, how to make photodynamic therapy and photoacoustic measurement be performed at the same time is actually one of the current problems that needs to be solved urgently.

SUMMARY OF THE DISCLOSURE

The present disclosure provides a system and method for simultaneously performing photodynamic therapy and photoacoustic measurement, which makes photodynamic therapy and photoacoustic measurement be performed at the same time. As a result, doctors may immediately monitor whether the tumor is cleared and make adjustments according to the treatment situation. This also results in a reduced waiting time for patients throughout the process, resulting in a smaller risk of illness.

The present disclosure provides a system for simultaneously performing photodynamic therapy and photoacoustic measurement, including: a pulsed light source, configured to emit a pulsed light; a light splitter, disposed on an optical path of the pulsed light, and configured to split the pulsed light into a first split light and a second split light; a reflector, disposed on an optical path of the first split light, and configured to reflect the first split light into a reflected light; a first lens, disposed on an optical path of the reflected light, and configured to refract the reflected light to an irradiated surface to form a first light spot; and a second lens, disposed on an optical path of the second split light, and configured to refract the second split light to the irradiated surface to form a second light spot; wherein a light-splitting ratio of the light splitter is equal to or greater than about 3/7 and equal to or less than about 1/2, the light-splitting ratio is a ratio between a power of the first split light and a power of the second split light.

In some embodiments, an average power density of the first light spot is equal to or greater than 40 $mW/cm^2$ and equal to or less than 200 $mW/cm^2$, or a pulse energy density of the first light spot is equal to or greater than 40 $mJ/cm^2$ and equal to or less than 200 $mJ/cm^2$.

In some embodiments, when the average power density of the first light spot is equal to or greater than 40 $mW/cm^2$ and equal to or less than 200 $mW/cm^2$, a pulse energy density of the second light spot is equal to or greater than 40 $mJ/cm^2$ and equal to or less than 200 $mJ/cm^2$; and when the pulse energy density of the first light spot is equal to or greater than 40 $mJ/cm^2$ and equal to or less than 200 $mJ/cm^2$, an average power density of the second light spot is equal to or greater than 40 $mW/cm^2$ and equal to or less than 200 $mW/cm^2$.

In some embodiments, a first diameter of the first light spot is about 5.5 mm or about 0.5 mm.

In some embodiments, when the first diameter of the first light spot is about 5.5 mm, a second diameter of the second light spot is about 0.5 mm; when the first diameter of the first light spot is about 0.5 mm, the second diameter of the second light spot is about 5.5 mm.

In some embodiments, a pulse repetition frequency of the pulsed light source is equal to or greater than 100 Hz and equal to or less than 10000 Hz.

In some embodiments, a pulse width of the pulsed light source is about 0.5 ms.

In some embodiments, a pulse power of the pulsed light source is about 225 mW.

The present disclosure provides a system for simultaneously performing photodynamic therapy and photoacoustic measurement, including: a pulsed light source, configured to emit a pulsed light; a light splitter, disposed on an optical path of the pulsed light, and configured to split the pulsed light into a first split light and a second split light; a first lens, disposed on an optical path of the first split light, and configured to refract the first split light into a refracted light; a reflector, disposed on an optical path of the refracted light, and configured to reflect the refracted light to an irradiated surface to form a first light spot; and a second lens, disposed on an optical path of the second split light, and configured to refract the second split light to the irradiated surface to form a second light spot; wherein a light-splitting ratio of the light splitter is equal to or greater than about 3/7 and equal to or less than about 1/2, the light-splitting ratio is a ratio between a power of the first split light and a power of the second split light.

In some embodiments, an average power density of the first light spot is equal to or greater than 40 $mW/cm^2$ and equal to or less than 200 $mW/cm^2$, or a pulse energy density of the first light spot is equal to or greater than 40 $mJ/cm^2$ and equal to or less than 200 $mJ/cm^2$.

In some embodiments, when the average power density of the first light spot is equal to or greater than 40 $mW/cm^2$ and equal to or less than 200 $mW/cm^2$, a pulse energy density of the second light spot is equal to or greater than 40 $mJ/cm^2$ and equal to or less than 200 $mJ/cm^2$; and when the pulse energy density of the first light spot is equal to or greater than 40 $mJ/cm^2$ and equal to or less than 200 $mJ/cm^2$, an average power density of the second light spot is equal to or greater than 40 $mW/cm^2$ and equal to or less than 200 $mW/cm^2$.

In some embodiments, a pulse power of the pulsed light source is about 225 mW.

The present disclosure provides a method for simultaneously performing photodynamic therapy and photoacoustic measurement, including: emitting a pulsed light; splitting the pulsed light into a first split light and a second split light; reflecting the first split light into a reflected light; refracting the reflected light to an irradiated surface to form a first light spot; and refracting the second split light to the irradiated surface to form a second light spot; wherein a ratio between a power of the first split light and a power of the second split light is equal to or greater than about 3/7 and equal to or less than about 1/2.

In some embodiments, the method for simultaneously performing photodynamic therapy and photoacoustic measurement, further including: refracting the reflected light to the irradiated surface to make an average power density of the first light spot be equal to or greater than 40 $mW/cm^2$ and equal to or less than 200 $mW/cm^2$, or refracting the reflected light to the irradiated surface to make a pulse energy density of the first light spot be equal to or greater than 40 $mJ/cm^2$ and equal to or less than 200 $mJ/cm^2$.

In some embodiments, the method for simultaneously performing photodynamic therapy and photoacoustic measurement, further including: when the reflected light is refracted to the irradiated surface to form the average power density of the first light spot is equal to or greater than 40 $mW/cm^2$ and equal to or less than 200 $mW/cm^2$, refracting the second split light to the irradiated surface to make a pulse energy density of the second light spot be about equal to or greater than 40 $mJ/cm^2$ and equal to or less than 200 $mJ/cm^2$; and when the reflected light is refracted to the irradiated surface to form the pulse energy density of the first light spot is equal to or greater than 40 $mJ/cm^2$ and equal to or less than 200 $mJ/cm^2$, refracting the second split light to the irradiated surface to make the average power density of the second light spot be equal to or greater than 40 $mW/cm^2$ and equal to or less than 200 $mW/cm^2$.

In some embodiments, the method for simultaneously performing photodynamic therapy and photoacoustic measurement, further including: refracting the reflected light to the irradiated surface with a first diameter of the first light spot being about 5.5 mm or about 0.5 mm.

In some embodiments, the method for simultaneously performing photodynamic therapy and photoacoustic measurement, further including: when the reflected light is refracted to the irradiated surface with the first diameter of the first light spot being about 5.5 mm, refracting the second split light to the irradiated surface with a second diameter of the second light spot is about 0.5 mm; and when the reflected light is refracted to the irradiated surface to form the first diameter of the first light spot is about 0.5 mm, refracting the second split light to the irradiated surface to form the second diameter of the second light spot is about 5.5 mm.

In some embodiments, the method for simultaneously performing photodynamic therapy and photoacoustic measurement, further including: emitting the pulsed light with a pulse repetition frequency of equal to or greater than 100 Hz and equal to or less than 10000 Hz.

In some embodiments, the method for simultaneously performing photodynamic therapy and photoacoustic measurement, further including: emitting the pulsed light with a pulse width of about 0.5 ms.

In some embodiments, the method for simultaneously performing photodynamic therapy and photoacoustic measurement, further including: emitting the pulsed light with a pulse power of about 225 mW.

In summary, the related-art of photodynamic therapy and photoacoustic measurement are processes that may not be performed at the same time. Therefore, the processes of treatment, measurement, and diagnosis need to be separated. As a result, doctors may not immediately monitor whether the tumor is cleared and make adjustments according to the treatment situation. This also results in an extended waiting time for patients throughout the process, resulting in a greater risk of illness. The present disclosure provides a system and method for simultaneously performing photodynamic therapy and photoacoustic measurement that makes a first light spot and a second light spot conform to specific parameters, causing photodynamic therapy and photoacoustic measurement at the same time. As a result, doctors may immediately monitor whether the tumor is cleared and make adjustments according to the treatment situation. This also results in a reduced waiting time for patients throughout the process, resulting in a smaller risk of illness.

DETAILED DESCRIPTION

The technical contents of this disclosure will become apparent with the detailed description of embodiments accompanied with the illustration of related drawings as follows. It is intended that the embodiments and drawings disclosed herein are to be considered illustrative rather than restrictive.

As used in the present disclosure, terms such as “first”, “second”, “third”, “fourth”, and “fifth” are employed to describe various elements, components, regions, layers, and/or parts. These terms should not be construed as limitations on the mentioned elements, components, regions, layers, and/or parts. Instead, they are used merely for distinguishing one element, component, region, layer, or part from another. Unless explicitly indicated in the context, the usage of terms such as “first”, “second”, “third”, “fourth”, and “fifth” does not imply any specific sequence or order.

Figure 1:
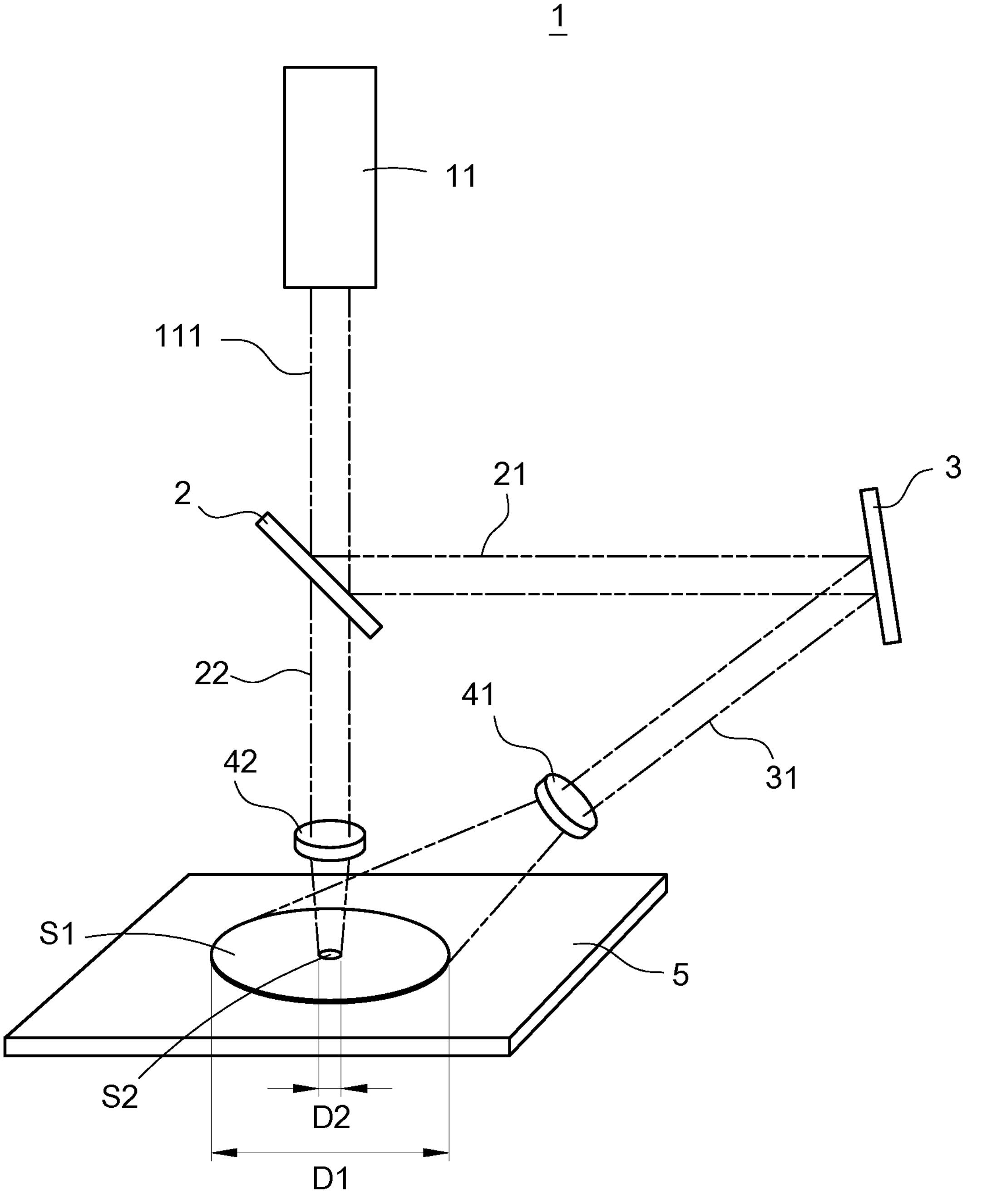
FIG. 1 is a schematic diagram of the system for simultaneously performing photodynamic therapy and photoacoustic measurement in accordance with some embodiments of the present disclosure.
Figure 2:
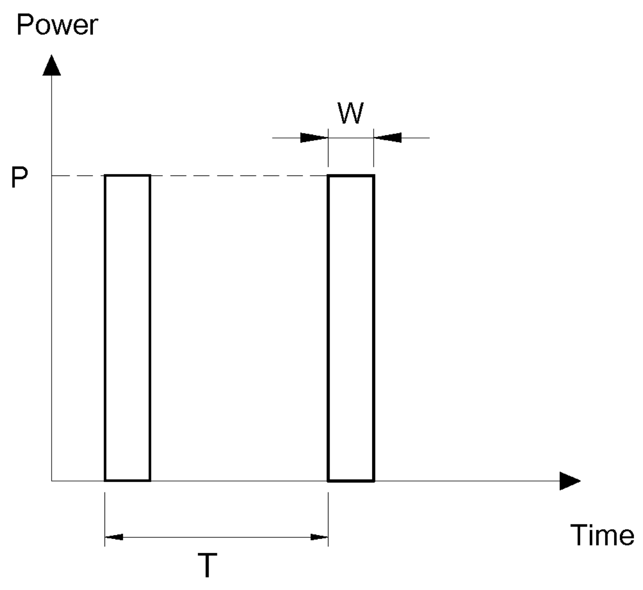
FIG. 2 is a schematic diagram of the laser parameters of the pulsed light source in accordance with the present disclosure.

FIG. 1 is a schematic diagram of the system for simultaneously performing photodynamic therapy and photoacoustic measurement in accordance with some embodiments of the present disclosure. FIG. 2 is a schematic diagram of the laser parameters of the pulsed light source 11 in accordance with the present disclosure. Please refer to FIG. 1 and FIG. 2, the present disclosure provides a system for simultaneously performing photodynamic therapy and photoacoustic measurement 1 includes a pulsed light source 11, a light splitter 2, a reflector 3, a first lens 41, and a second lens 42.

The pulsed light source 11 is configured to emit a pulsed light 111. The pulsed light 111 is a high-energy light pulse that is released in a very short period. These pulses may release a large amount of energy in one very narrow window of time, often in milliseconds or less. The emission mechanism of the pulsed light source 11 may be, for example, an electron cyclotron maser or laser. In the embodiment, the pulsed light source 11 is a laser light source, here is not intended to be limiting. The wavelength of the electromagnetic wave emitted by the pulsed light source 11 may be, for example, equal to or greater than about 600 nm and equal to or less than about 1300 nm. This band is suitable for use in phototherapy windows. In the embodiment, the wavelength of the electromagnetic wave emitted by the pulsed light source 11 is equal to or greater than about 600 nm and equal to or less than about 800 nm, and the depth of penetration into the skin is equal to or greater than about 4 mm and equal to or less than about 5 mm, which is suitable for the photodynamic therapy, here is not intended to be limiting. In some embodiments, a pulse repetition frequency of the pulsed light source 11 is about 475 Hz. The pulse repetition frequency is the number of pulses emitted per unit time. When the pulse repetition frequency is about 475 Hz, the photodynamic therapy has better singlet oxygen production, and the photodynamic therapy has better effects. In some embodiments, the pulse width w of the pulsed light source 11 is about 0.5 ms. The pulse width w is the time duration of a single pulse. When the pulse width w is about 0.5 ms, the photoacoustic effect is better. In some embodiments, a pulse power P of the pulsed light source 11 is about 225 mW. The pulse power P is the power of a single pulse. The pulse power P of the pulsed light source 11 about 225 mW is suitable for simultaneously performing photodynamic therapy and photoacoustic measurement.

A light splitter 2 is disposed on an optical path of the pulsed light 111, and configured to split the pulsed light 111 into a first split light 21 and a second split light 22. The light splitter 2 may be, for example, a spectroscope, a polarizing beam splitter, or a beam splitter, here is not intended to be limiting. The light splitter 2 is used to split the pulsed light 111 emitted by the pulsed light source 11 into a first split light 21 and a second split light 22. In some embodiments, a light-splitting ratio of the light splitter 2 is equal to or greater than about 3/7 and equal to or less than about 1/2, the light-splitting ratio is a ratio between a power of the first split light 21 and a power of the second split light 22. For example, the power of the first split light 21 is 67.5 mW, and the power of the second split light 22 is 157.5 mW; or the power of the first split light 21 is 75 mW, and the power of the second split light 22 is 150 mW, which makes the first split light 21 be suitable as a light source for the photodynamic therapy and the second split light 22 be suitable as a light source for the photoacoustic measurement. For example, the power of the first split light 21 is 157.5 mW, and the power of the second split light 22 is 67.5 mW; or the power of the first split light 21 is 150 mW, and the power of the second split light 22 is 75 mW, which makes the first split light 21 be suitable as a light source for the photoacoustic measurement and the second split light 22 be suitable as a light source for the photodynamic therapy.

A reflector 3 is disposed on an optical path of the first split light 21, and configured to reflect the first split light 21 into a reflected light 31. The reflector 3 may be, for example, a mirror, a prism, or a metal mirror, here is not intended to be limiting. The reflector 3 is used to reflect the first split light 21 into a reflected light 31 to change the direction of the light.

A first lens 41 is disposed on an optical path of the reflected light 31, and configured to refract the reflected light 31 to an irradiated surface 5 to form a first light spot S1. The first lens 41 may be, for example, a convex lens or a concave lens. The material of the first lens 41 may be, for example, glass or plastic, here is not intended to be limiting. The first lens 41 is used to refract the reflected light 31 to an irradiated surface 5, to converge or diverge the light to the irradiated surface 5, to be a first light spot S1.

A second lens 42 is disposed on an optical path of the second split light 22, and configured to refract the second split light 22 to the irradiated surface 5 to form a second light spot S2. The second lens 42 may be, for example, a convex lens or a concave lens. The material of the second lens 42 may be, for example, glass or plastic, here is not intended to be limiting. The second lens 42 is used to refract the second split light 22 to the irradiated surface 5, to converge or diverge the light to the irradiated surface 5, to be a second light spot S2. In this embodiment, the first light spot S1 is used for the photodynamic therapy purpose, and the second light spot S2 is used for the photoacoustic measurement purpose. When an average power density of the first light spot S1 is equal to or greater than 40 mW/cm$^2$ and equal to or less than 200 mW/cm$^2$, it is suitable for the photodynamic therapy. The average power density of the first light spot S1 is the total energy per unit area per unit time in the first light spot S1. The average power density may be expressed, for example, by formula 1 or formula 2:

$$\text{the average power density} = \frac{P \times w}{\pi \times \left(\frac{D}{2}\right)^2} \times \frac{1}{T} \quad \text{Formula 1}$$

$$\text{the average power density} = \frac{P \times w}{\pi \times \left(\frac{D}{2}\right)^2} \times f \quad \text{Formula 2}$$

P is the pulse power P of the laser light source, w is the pulse width w of the laser light source w, π is pi, D is the first diameter D1 of the first light spot S1, T is the pulse repetition period T of the laser light source, and f is the pulse repetition frequency of the laser light source.

For example, the power of the first split light 21 is 75 mW, the pulse width w is 0.5 ms, the pulse repetition frequency is about 475 Hz, and the first light spot S1 is the first diameter D1 is 5.5 mm, to make $$\text{the average power density} = \frac{75\ \text{mW} \times 0.5\ \text{ms}}{\pi \times \left(\frac{5.5\ \text{mm}}{2}\right)^2} \times 475\ \text{Hz} = 75\ \text{mW/cm}^2.$$

In other embodiments, when the average power density of the first light spot S1 is about 67.5 mW/cm$^2$, it may also be used for the photodynamic therapy. For example, the power of the first split light 21 is 67.5 mW, the pulse width w is 0.5 ms, the pulse repetition frequency is about 475 Hz, and the first diameter D1 of the first light spot S1 is 5.5 mm, to make $$\text{the average power density} = \frac{67.5\ \text{mW} \times 0.5\ \text{ms}}{\pi \times \left(\frac{5.5\ \text{mm}}{2}\right)^2} \times 475\ \text{Hz} = 67.5\ \text{mW/cm}^2.$$

When the average power density of the first light spot S1 is equal to or greater than 40 mW/cm$^2$ and equal to or less than 200 mW/cm$^2$, a pulse energy density of the second light spot S2 is equal to or greater than 40 mJ/cm$^2$ and equal to or less than 200 mJ/cm$^2$. The pulse energy density of the second light spot S2 is the total energy of a single pulse per unit area in the second light spot S2. The pulse energy density may be expressed, for example, by formula 3:

$$\text{the pulse energy density} = \frac{P \times w}{\pi \times \left(\frac{D}{2}\right)^2} \qquad \text{Formula 3}$$

When the average power density of the second light spot S2 is 76.4 mW/cm$^2$, there is a better the photoacoustic measurement effect. For example, the power of the second split light 22 is 150 mW, the pulse width w is 0.5 ms, the pulse repetition frequency is about 475 Hz, and the second diameter D2 of the second light spot S2 is 0.5 mm, to make $$\text{the pulse energy density} = \frac{150\ \text{mW} \times 0.5\ \text{ms}}{\pi \times \left(\frac{0.5\ \text{mm}}{2}\right)^2} = 38.2\ \text{mJ/cm}^2.$$

In other embodiments, when the average power density of the second light spot S2 is 80.2 mJ/cm$^2$, it may also be used for the photodynamic therapy. For example, the power of the second split light 22 is 157.5 mW, the pulse width w is 0.5 ms, the pulse repetition frequency is about 475 Hz, and the second diameter D2 of the second light spot S2 is 0.5 mm, to make $$\text{the pulse energy density} = \frac{157.5\ \text{mW} \times 0.5\ \text{ms}}{\pi \times \left(\frac{0.5\ \text{mm}}{2}\right)^2} = 40.1\ \text{mJ/cm}^2.$$

In this embodiment, the first light spot S1 is used for the photoacoustic measurement purpose, and the second light spot S2 is used for the photodynamic therapy purpose. When the average power density of the first light spot S1 is equal to or greater than 40 mJ/cm$^2$ and equal to or less than 200 mJ/cm$^2$, there is a better the photoacoustic measurement effect. For example, the power of the first split light 21 is 150 mW, the pulse width w is 0.5 ms, the pulse repetition frequency is about 475 Hz, and the first diameter D1 of the first light spot S1 is 0.5 mm, to make $$\text{the pulse energy density} = \frac{150\ \text{mW} \times 0.5\ \text{ms}}{\pi \times \left(\frac{0.5\ \text{mm}}{2}\right)^2} = 38.2\ \text{mJ/cm}^2.$$

In other embodiments, when the average power density of the first light spot S1 is 80.2 mJ/cm$^2$, it may also be used for the photodynamic therapy. For example, the power of the first split light 21 is 157.5 mW, the pulse width w is 0.5 ms, the pulse repetition frequency is about 475 Hz, and the first diameter D1 of the first light spot S1 is 0.5 mm, to make $$\text{the pulse energy density} = \frac{157.5\ \text{mW} \times 0.5\ \text{ms}}{\pi \times \left(\frac{0.5\ \text{mm}}{2}\right)^2} = 40.1\ \text{mJ/cm}^2.$$

When the pulse energy density of the first light spot S1 is equal to or greater than 40 mJ/cm$^2$ and equal to or less than 200 mJ/cm$^2$, an average power density of the second light spot S2 is equal to or greater than 40 mW/cm$^2$ and equal to or less than 200 mW/cm$^2$, it is suitable for the photodynamic therapy. For example, the power of the second split light 22 is 75 mW, the pulse width w is 0.5 ms, the pulse repetition frequency is about 475 Hz, and the second light spot S2 is the second diameter D2 is 5.5 mm, to make $$\text{the average power density} = \frac{75\ \text{mW} \times 0.5\ \text{ms}}{\pi \times \left(\frac{5.5\ \text{mm}}{2}\right)^2} \times 475\ \text{Hz} = 75\ \text{mW/cm}^2.$$

In other embodiments, when the average power density of the second light spot S2 is about 67.5 mW/cm$^2$, it may also be used for the photodynamic therapy. For example, the power of the second split light 22 is 67.5 mW, the pulse width w is 0.5 ms, the pulse repetition frequency is about 475 Hz, and the second diameter D2 of the second light spot S2 is 5.5 mm, to make $$\text{the average power density} = \frac{67.5\ \text{mW} \times 0.5\ \text{ms}}{\pi \times \left(\frac{5.5\ \text{mm}}{2}\right)^2} \times 475\ \text{Hz} = 67.5\ \text{mW/cm}^2.$$

It is worth mentioning that the laser should avoid direct irradiation into the eyes. If the laser irradiates into the eyes, the laser may result in irreversible damage to the retina. When the laser irradiates on human skin, the energy density of the laser also needs to be controlled to avoid excessive energy density irradiation that may damage the skin tissue. The maximum permissible exposure is a condition that needs to be met within the range. The MPE calculation method corresponding to laser specifications may be found from the American national standard for safe use of lasers to determine the maximum laser energy density that may be used. When a wavelength of the laser is in the range of 400 nm to 1,400 nm, the MPE calculation formula is as follows formula 1. Table 1 shows the correction coefficients for calculating MPE.

$$MPE(t) = \begin{cases} 2C_A \times 10^{-2},\ 10^{-9} \le t < 10^{-7}\ \text{(seconds)} \\ 1.1C_A \times t^{0.25},\ 10^{-7} \le t < 10\ \text{(seconds)} \\ 0.2C_A,\ 10 \le t < 3 \times 10^4\ \text{(seconds)} \end{cases} \quad \text{Formula 4}$$

TABLE 1

| |
|---|
| $C_A = 1.0,\ 400 \le \lambda < 700$ |
| $C_A = 10^{2(\lambda-0.7)},\ 700 \le \lambda < 1{,}050$ |
| $C_A = 5.0,\ 1{,}050 \le \lambda < 1{,}400$ |

MPE is the energy density in J/cm$^2$; $C_A$ is the correction coefficient; t is the laser exposure time in seconds; λ is the wavelength in nm. The laser parameters used in the present disclosure are all in compliance with MPE standards.

Figure 3:
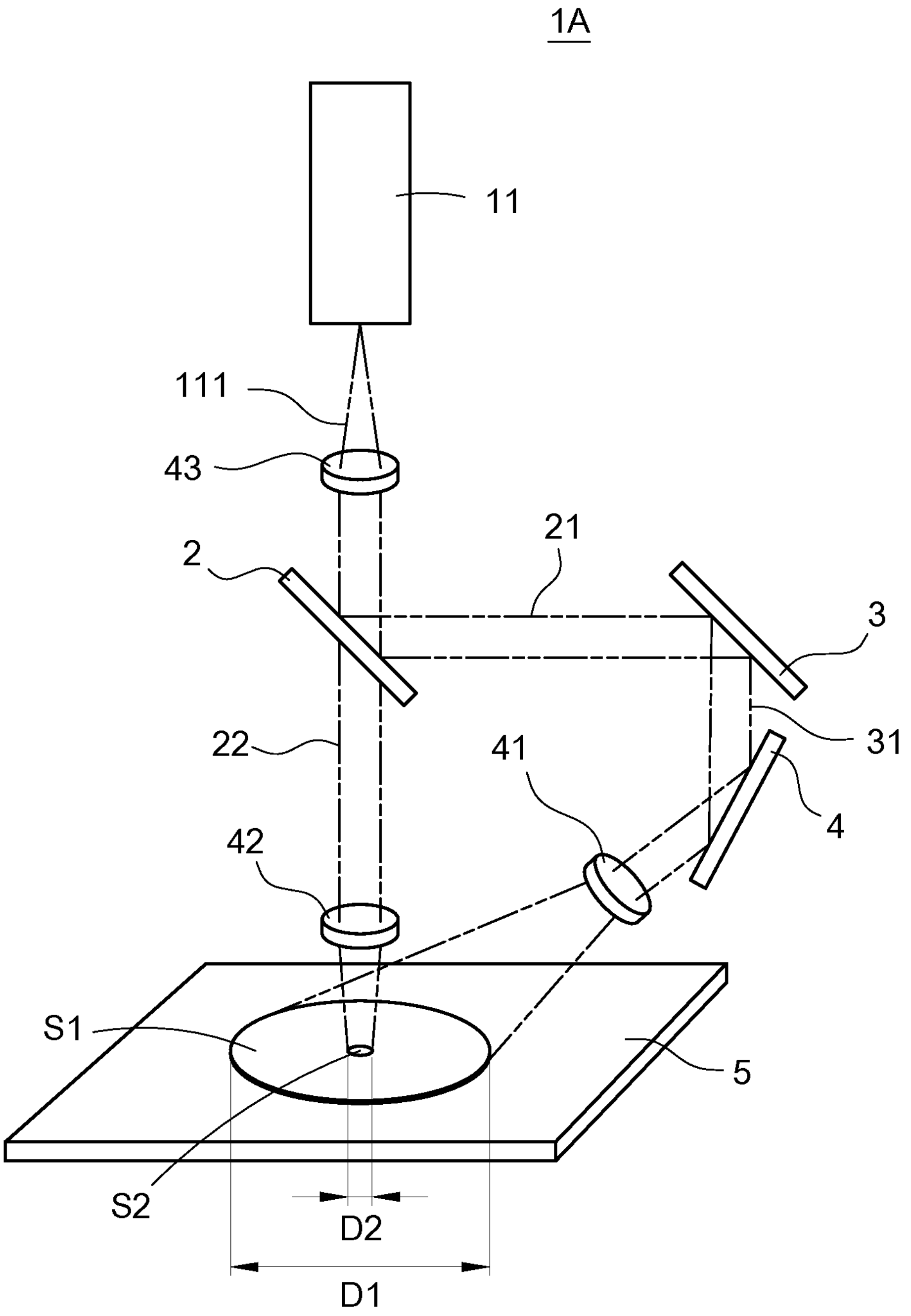
FIG. 3 is a schematic diagram of the system for simultaneously performing photodynamic therapy and photoacoustic measurement in accordance with some embodiments of the present disclosure.

FIG. 3 is a schematic diagram of the system for simultaneously performing photodynamic therapy and photoacoustic measurement in accordance with some embodiments of the present disclosure. Please refer to FIG. 3, a system for simultaneously performing photodynamic therapy and photoacoustic measurement 1A of FIG. 3 is similar to the system for simultaneously performing photodynamic therapy and photoacoustic measurement 1 of FIG. 1. The difference is that a system for simultaneously performing photodynamic therapy and photoacoustic measurement 1A of FIG. 3 further includes a third lens 43 and a reflector 4.

The third lens 43 is disposed on the optical path of the pulsed light 111 and configured to refract the pulsed light 111. The third lens 43 may be, for example, a convex lens or a concave lens. The material of the third lens 43 may be, for example, glass or plastic, here is not intended to be limiting. The third lens 43 is used to converge the pulsed light 111 to parallel light.

The reflector 4 is disposed on the light path of the reflected lights 31, and configured to reflect the reflected lights 31. The reflector 4 may be, for example, a mirror, a prism, or a metal mirror, here is not intended to be limiting. The reflector 4 is used to reflect the reflected lights 31 to change the direction of light.

In summary, the related-art of photodynamic therapy and photoacoustic measurement are processes that may not be performed at the same time. Therefore, the processes of treatment, measurement, and diagnosis need to be separated. As a result, doctors may not immediately monitor whether the tumor is cleared and make adjustments according to the treatment situation. This also results in an extended waiting time for patients throughout the process, resulting in a greater risk of illness. The photodynamic therapy and photoacoustic measurement be performed at the same time through a system for simultaneously performing photodynamic therapy and photoacoustic measurement 1, 1A of the present disclosure by specifying the parameters of the pulsed light source 11, specifying the light-splitting ratio of the light splitter 2, adjusting the light path through the reflector 3, adjusting the diameter, the average power density and the pulse energy density of the light spots by the first lens 41 and the second lens 42. In some embodiments, the light path may be adjusted by the third lens 43 and the reflector 4. As a result, doctors may immediately monitor whether the tumor is cleared and make adjustments according to the treatment situation. This also results in a reduced waiting time for patients throughout the process, resulting in a smaller risk of illness.

Figure 4:
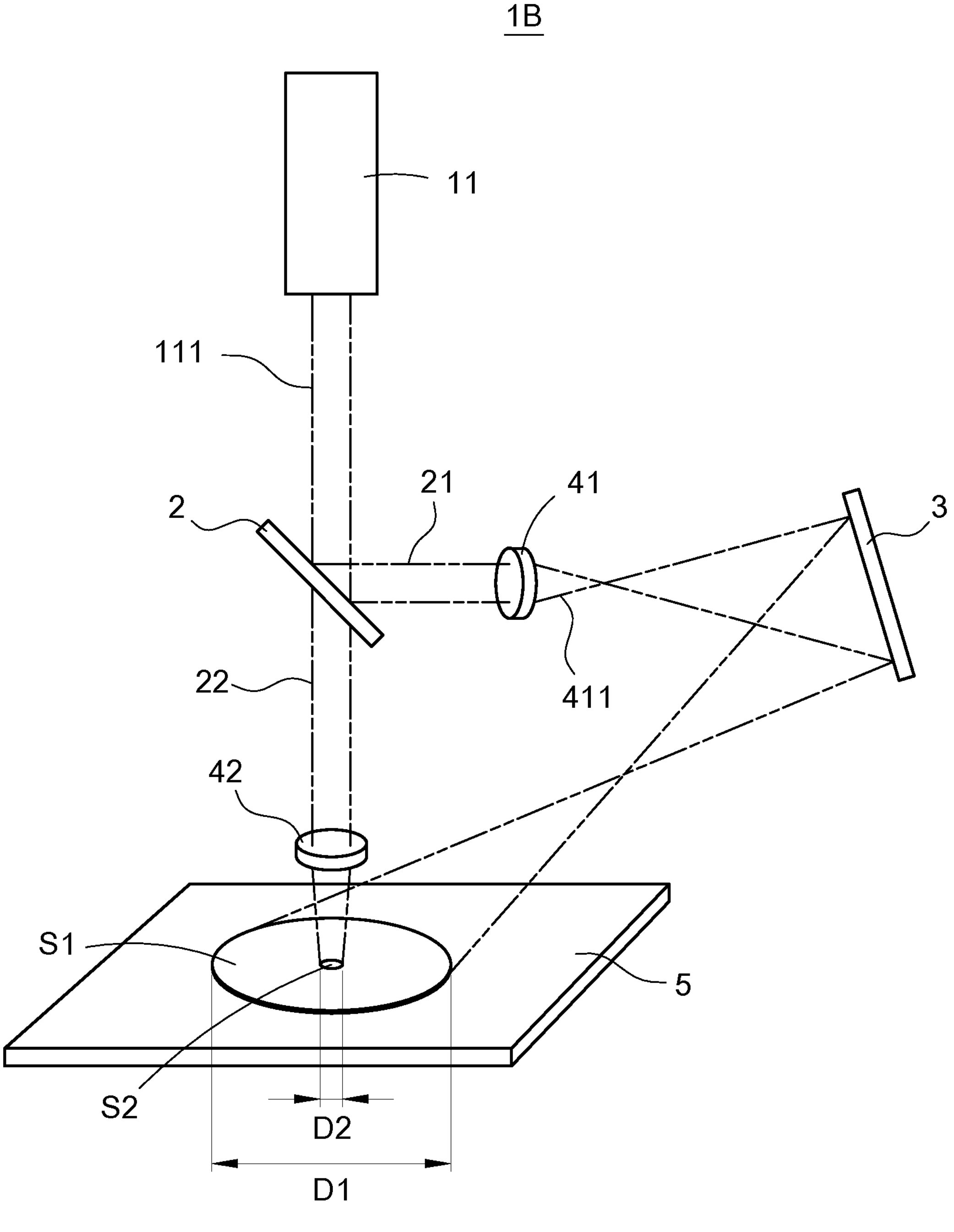
FIG. 4 is a schematic diagram of the system for simultaneously performing photodynamic therapy and photoacoustic measurement in accordance with some embodiments of the present disclosure.

FIG. 4 is a schematic diagram of the system for simultaneously performing photodynamic therapy and photoacoustic measurement 1B in accordance with some embodiments of the present disclosure. Please refer to FIG. 2 and FIG. 4, a system for simultaneously performing photodynamic therapy and photoacoustic measurement 1B of FIG. 4 is similar to the system for simultaneously performing photodynamic therapy and photoacoustic measurement 1 of FIG. 1. The difference is that a first lens 41 and a reflector 3 of the system for simultaneously performing photodynamic therapy and photoacoustic measurement 1B of FIG. 4 are disposed on the different positions. A pulsed light source 11, and a light splitter 2 and a second lens 42 are similar to the system for simultaneously performing photodynamic therapy and photoacoustic measurement 1 of FIG. 1, here is omitted for brevity.

The first lens 41 is disposed on the optical path of a first split light 21 and configured to refract the first split light 21 to the refracted light 411. The first lens 41 may be, for example, a convex lens or a concave lens. The material of the first lens 41 may be, for example, glass or plastic, here is not intended to be limiting. The first lens 41 is used to refract the first split light 21 to converge or diverge the light.

The reflector 3 is disposed on the light path of the refracted light 411 and configured to reflect the refracted light 411 to the irradiated surface 5 to form the first light spot S1. The reflector 3 may be, for example, a mirror, a prism, or a metal mirror, here is not intended to be limiting. The reflector 3 is used to reflect the refracted light 411 to the irradiated surface 5, to form the first light spot S1.

In some embodiments, the pulse power P of the pulsed light source 11 is about 225 mW which is similar to the system for simultaneously performing photodynamic therapy and photoacoustic measurement 1 of FIG. 1, here is omitted for brevity.

In some embodiments, the average power density of the first light spot S1 is equal to or greater than 40 mW/cm$^2$ and equal to or less than 200 mW/cm$^2$, or the pulse energy density of the first light spot S1 is equal to or greater than 40 mJ/cm$^2$ and equal to or less than 200 mJ/cm$^2$ which are similar to the system for simultaneously performing photodynamic therapy and photoacoustic measurement 1 of FIG. 1, here is omitted for brevity.

In some embodiments, when the average power density of the first light spot S1 is equal to or greater than 40 mW/cm$^2$ and equal to or less than 200 mW/cm$^2$, a pulse energy density of the second light spot S2 is equal to or greater than 40 mJ/cm$^2$ and equal to or less than 200 mJ/cm$^2$, or when the pulse energy density of the first light spot S1 is equal to or greater than 40 mJ/cm$^2$ and equal to or less than 200 mJ/cm$^2$, an average power density of the second light spot S2 is equal to or greater than 40 mW/cm$^2$ and equal to or less than 200 mW/cm$^2$, which are similar to the system for simultaneously performing photodynamic therapy and photoacoustic measurement 1 of FIG. 1, here is omitted for brevity.

As a result, different configurations of the system for simultaneously performing photodynamic therapy and photoacoustic measurement are added to increase the scope of application.

Figure 5:
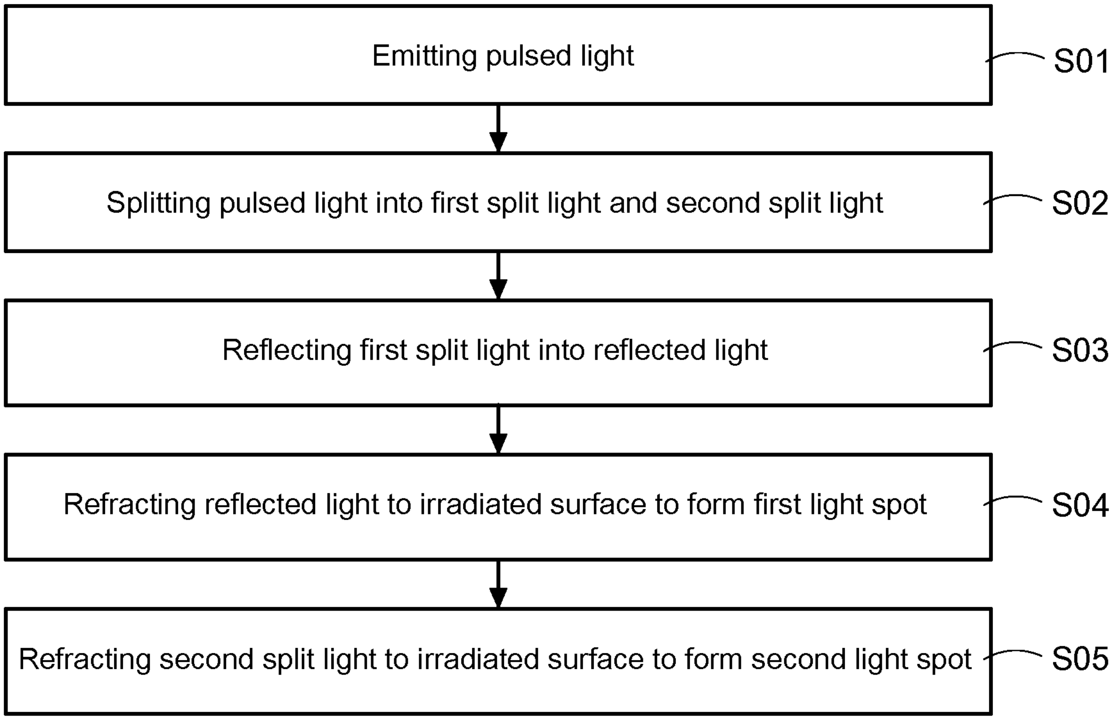
FIG. 5 is a flowchart of the method for simultaneously performing photodynamic therapy and photoacoustic measurement in accordance with some embodiments of the present disclosure.

FIG. 5 is a flowchart of the method for simultaneously performing photodynamic therapy and photoacoustic measurement in accordance with some embodiments of the present disclosure, please refer to FIG. 5, the step S01 is emitting a pulsed light; the step S02 is splitting the pulsed light into a first split light, and a second split light; the step S03 is reflecting the first split light into a reflected light; the step S04 is refracting the reflected light to an irradiated surface to form a first light spot; and the step S05 is refracting the second split light to the irradiated surface to form a second light spot. It is worth mentioning that the present disclosure of a method for simultaneously performing photodynamic therapy and photoacoustic measurement may cooperate with the system for simultaneously performing photodynamic therapy and photoacoustic measurement 1 of FIG. 1, here is not intended to be limiting.

Please refer to FIG. 1, FIG. 2, and FIG. 5, the step S01 is emitting a pulsed light 111. The emission mechanism may be, for example, an electron cyclotron maser or laser. In the embodiment, a laser light source is used to emit laser light, here is not intended to be limiting. For example, the wavelength of the electromagnetic wave emitting a pulsed light 111 is equal to or greater than about 600 nm and equal to or less than about 1300 nm. This band is suitable for use in phototherapy windows. In the embodiment, the wavelength of the electromagnetic wave emitting a pulsed light 111 is equal to or greater than about 600 nm and equal to or less than about 800 nm, and the depth of penetration into the skin is about equal to or greater than 4 mm and equal to or less than 5 mm, which is suitable for photodynamic therapy, here is not intended to be limiting. In some embodiments, the pulsed light 111 with a pulse repetition frequency of about 475 Hz is emitted, resulting in better singlet oxygen production during photodynamic therapy and better photodynamic therapy effect. In some embodiments, emitting the pulsed light 111 with a pulse width w of about 0.5 ms results in a better photoacoustic effect. In some embodiments, emitting the pulsed light 111 with a pulse power P of about 225 mW is suitable for simultaneously performing photodynamic therapy and photoacoustic measurement. In the step 02 splitting the pulsed light 111 into a first split light 21 and a second split light 22.

The embodiment, for example, the pulsed light 111 may be split into the first split light 21 and the second split light 22 by a spectroscope, a polarizing beam splitter, or a beam splitter. In some embodiment, after the pulsed light 111 is split, a ratio between a power of the first split light 21 and a power of the second split light 22 is equal to or greater than about 3/7 and equal to or less than about 1/2. For example, the power of the first split light 21 is 67.5 mW, and the power of the second split light 22 is 157.5 mW, or the power of the first split light 21 is 75 mW, and the power of the second split light 22 is 150 mW, or the power of the first split light 21 is 157.5 mW, and the power of the second split light 22 is 67.5 mW, or the power of the first split light 21 is 150 mW, and the power of the second split light 22 is 75 mW, which is suitable for simultaneously performing photodynamic therapy and photoacoustic measurement.

The step S03 is reflecting the first split light 21 into a reflected light 31. The first split light 21 may be reflected through the reflector 3 such as a mirror, a prism, or a metal mirror. The angle of the reflected light 31 may be adjusted by adjusting the reflector 3.

The S04 is refracting the reflected light 31 to an irradiated surface 5 to form a first light spot S1. The size of the first light spot S1 of the first diameter D1 on the irradiated surface 5 may be controlled, for example, by selecting the focal length of the lens, and adjusting the position of the lens.

The step S05 is refracting the second split light 22 to the irradiated surface 5 to form a second light spot S2. The size of the second light spot S2 of the second diameter D2 on the irradiated surface 5 may be controlled, for example, by selecting the focal length of the lens, and adjusting the position of the lens.

In this embodiment, the first light spot S1 is used for the photodynamic therapy purpose, and the second light spot S2 is used for the photoacoustic measurement purpose. In this embodiment, refracting the reflected light 31 to the irradiated surface 5 to form the first light spot S1, further including: refracting the reflected light 31 to the irradiated surface 5 to make an average power density of the first light spot S1 be 75 mW/cm$^2$. For example, emitting the pulsed light 111 with the pulse power P of 225 mW, the pulse width w of 0.5 ms, the pulse repetition frequency of 475 Hz; then adjusting the ratio between the power of the first split light 21 and the power of the second split light 22 to 1/2; then selecting the focal length of the lens, and adjusting the position of the lens, to refract the reflected light 31 to the irradiated surface 5, result in the first diameter D1 of the first light spot S1 is about 5.5 mm. As a result, the average power density of the first light spot S1 is $$\frac{225\ \text{mW} \times \frac{1}{(1+2)} \times 0.5\ \text{ms}}{\pi \times \left(\frac{5.5\ \text{mm}}{2}\right)^2} \times 475\ \text{Hz} = 75\ \text{mW/cm}^2.$$

In the embodiment, refracting the second split light 22 to the irradiated surface 5 to form the second light spot S2, further including: when the reflected light 31 is refracted to the irradiated surface 5 to form the average power density of the first light spot S1 is 75 mW/cm$^2$, refracting the second split light 22 to the irradiated surface 5 to make the pulse energy density of the second light spot S2 be 76.4 mJ/cm$^2$. For example, emitting the pulsed light 111 with the pulse power P of 225 mW, the pulse width w of 0.5 ms, the pulse repetition frequency of 475 Hz; then adjusting the ratio between the power of the first split light 21 and the power of the second split light 22 to 1/2; then selecting the focal length of the lens, and adjusting the position of the lens, to refract the second split light 22 to the irradiated surface 5, result in the second diameter D2 of the second light spot S2 is about 0.5 mm. As a result, the pulse energy density of the second light spot S2 is $$\frac{225\ \text{mW} \times \frac{2}{(1+2)} \times 0.5\ \text{ms}}{\pi \times \left(\frac{0.5\ \text{mm}}{2}\right)^2} = 38.2\ \text{mJ/cm}^2.$$

In this embodiment, the first light spot S1 is used for the photoacoustic measurement purpose, and the second light spot S2 is used for the photodynamic therapy purpose. In this embodiment, refracting the reflected light 31 to the irradiated surface 5 to form the first light spot S1, further including: refracting the reflected light 31 to the irradiated surface 5 to make the pulse energy density of the first light spot S1 be 76.4 mJ/cm$^2$. For example, emitting the pulsed light 111 with the pulse power P of 225 mW, the pulse width w of 0.5 ms, the pulse repetition frequency of 475 Hz; then adjusting the ratio between the power of the first split light 21 and the power of the second split light 22 to 1/2; then selecting the focal length of the lens, and adjusting the position of the lens, to refract the reflected light 31 to the irradiated surface 5, result in the first diameter D1 of the first light spot S1 is about 0.5 mm. As a result, the pulse energy density of the first light spot S1 is $$\frac{225\ \text{mW} \times \frac{2}{(1+2)} \times 0.5\ \text{ms}}{\pi \times \left(\frac{0.5\ \text{mm}}{2}\right)^2} = 38.2\ \text{mJ/cm}^2.$$

In the embodiment, refracting the second split light 22 to the irradiated surface 5 to form the second light spot S2, further including: when the reflected light 31 is refracted to the irradiated surface 5 to form the pulse energy density of the first light spot S1 is 76.4 mJ/cm$^2$, refracting the second split light 22 to the irradiated surface 5 to make the average power density of the second light spot S2 be 75 mW/cm$^2$. For example, emitting the pulsed light 111 with the pulse power P of 225 mW, the pulse width w of 0.5 ms, the pulse repetition frequency of 475 Hz; then adjusting the ratio between the power of the first split light 21 and the power of the second split light 22 to 1/2; then selecting the focal length of the lens, and adjusting the position of the lens, to refract the second split light 22 to the irradiated surface 5, result in the second diameter D2 of the second light spot S2 is about 5.5 mm. As a result, the average power density of the second light spot S2 is $$\frac{225\ \text{mW} \times \frac{1}{(1+2)} \times 0.5\ \text{ms}}{\pi \times \left(\frac{5.5\ \text{mm}}{2}\right)^2} \times 475\ \text{Hz} = 75\ \text{mW/cm}^2.$$

In summary, the related-art of photodynamic therapy and photoacoustic measurement are processes that may not be performed at the same time. Therefore, the processes of treatment, measurement, and diagnosis need to be separated. As a result, doctors may not immediately monitor whether the tumor is cleared and make adjustments according to the treatment situation. This also results in an extended waiting time for patients throughout the process, resulting in a greater risk of illness. The present disclosure provides a system and method for simultaneously performing photodynamic therapy and photoacoustic measurement that makes a first light spot and a second light spot conform to specific parameters, causing photodynamic therapy and photoacoustic measurement at the same time. As a result, doctors may immediately monitor whether the tumor is cleared and make adjustments according to the treatment situation. This also results in a reduced waiting time for patients throughout the process, resulting in a smaller risk of illness.

As used herein and not otherwise defined, the terms “substantially” and “approximately” are used to describe and account for small variations. When used in conjunction with an event or circumstance, the terms may refer to instances in which the event or circumstance occurs precisely as well as instances in which the event or circumstance occurs to a close approximation. For example, when used in conjunction with a numerical value, the terms may refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

While this disclosure has been described by means of specific embodiments, numerous modifications and variations may be made thereto by those skilled in the art without departing from the scope and spirit of this disclosure set forth in the claims.

What is claimed is:

1. A system for simultaneously performing photodynamic therapy and photoacoustic measurement, comprising:

a pulsed light source, configured to emit a pulsed light;

a light splitter, disposed on an optical path of the pulsed light, and configured to split the pulsed light into a first split light and a second split light;

a reflector, disposed on an optical path of the first split light, and configured to reflect the first split light into a reflected light;

a first lens, disposed on an optical path of the reflected light, and configured to refract the reflected light to an irradiated surface to form a first light spot; and a second lens, disposed on an optical path of the second split light, and configured to refract the second split light to the irradiated surface to form a second light spot;

wherein a light-splitting ratio of the light splitter is equal to or greater than about 3/7 and equal to or less than about 1/2, the light-splitting ratio is a ratio between a power of the first split light and a power of the second split light;

one of the first light spot and the second light spot is used for the photodynamic therapy, and an average power density of the one is equal to or greater than 40 mW/cm$^2$ and equal to or less than 200 mW/cm$^2$;

the other of the first light spot and the second light spot is used for the photoacoustic measurement, and a pulse energy density of the other is equal to or greater than 40 mJ/cm$^2$ and equal to or less than 200 mJ/cm$^2$.

2. The system for simultaneously performing photodynamic therapy and photoacoustic measurement of claim 1, wherein, a first diameter of the first light spot is about 5.5 mm or about 0.5 mm.

3. The system for simultaneously performing photodynamic therapy and photoacoustic measurement of claim 2, wherein, when the first diameter of the first light spot is about 5.5 mm, a second diameter of the second light spot is about 0.5 mm; when the first diameter of the first light spot is about 0.5 mm, the second diameter of the second light spot is about 5.5 mm.

4. The system for simultaneously performing photodynamic therapy and photoacoustic measurement of claim 1, wherein, a pulse repetition frequency of the pulsed light source is equal to or greater than 100 Hz and equal to or less than 10000 Hz.

5. The system for simultaneously performing photodynamic therapy and photoacoustic measurement of claim 1, wherein, a pulse width of the pulsed light source is about 0.5 ms.

6. The system for simultaneously performing photodynamic therapy and photoacoustic measurement of claim 1, wherein, a pulse power of the pulsed light source is about 225 mW.

7. A system for simultaneously performing photodynamic therapy and photoacoustic measurement, comprising:

a pulsed light source, configured to emit a pulsed light;

a light splitter, disposed on an optical path of the pulsed light, and configured to split the pulsed light into a first split light and a second split light;

a first lens, disposed on an optical path of the first split light, and configured to refract the first split light into a refracted light;

a reflector, disposed on an optical path of the refracted light, and configured to reflect the refracted light to an irradiated surface to form a first light spot; and a second lens, disposed on an optical path of the second split light, and configured to refract the second split light to the irradiated surface to form a second light spot;

wherein a light-splitting ratio of the light splitter is equal to or greater than about 3/7 and equal to or less than about 1/2, the light-splitting ratio is a ratio between a power of the first split light and a power of the second split light;

one of the first light spot and the second light spot is used for the photodynamic therapy, and an average power density of the one is equal to or greater than 40 $mW/cm^2$ and equal to or less than 200 $mW/cm^2$;

the other of the first light spot and the second light spot is used for the photoacoustic measurement, and a pulse energy density of the other is equal to or greater than 40 $mJ/cm^2$ and equal to or less than 200 $mJ/cm^2$.

8. The system for simultaneously performing photodynamic therapy and photoacoustic measurement of claim 7, wherein, a pulse power of the pulsed light source is about 225 mW.

9. A method for simultaneously performing photodynamic therapy and photoacoustic measurement, comprising:

emitting a pulsed light;

splitting the pulsed light into a first split light and a second split light;

reflecting the first split light into a reflected light;

refracting the reflected light to an irradiated surface to form a first light spot; and refracting the second split light to the irradiated surface to form a second light spot;

wherein a ratio between a power of the first split light and a power of the second split light is equal to or greater than about 3/7 and equal to or less than about 1/2;

one of the first light spot and the second light spot is used for the photodynamic therapy, and an average power density of the one is equal to or greater than 40 $mW/cm^2$ and equal to or less than 200 $mW/cm^2$;

the other of the first light spot and the second light spot is used for the photoacoustic measurement, and a pulse energy density of the other is equal to or greater than 40 $mJ/cm^2$ and equal to or less than 200 $mJ/cm^2$.

10. The method for simultaneously performing photodynamic therapy and photoacoustic measurement of claim 9, wherein refracting the reflected light to the irradiated surface to form the first light spot, further comprising:

refracting the reflected light to the irradiated surface with a first diameter of the first light spot being about 5.5 mm or about 0.5 mm.

11. The method for simultaneously performing photodynamic therapy and photoacoustic measurement of claim 10, wherein refracting the second split light to the irradiated surface to form the second light spot, further comprising:

when the reflected light is refracted to the irradiated surface with the first diameter of the first light spot being about 5.5 mm, refracting the second split light to the irradiated surface with a second diameter of the second light spot is about 0.5 mm; and when the reflected light is refracted to the irradiated surface to form the first diameter of the first light spot is about 0.5 mm, refracting the second split light to the irradiated surface to form the second diameter of the second light spot is about 5.5 mm.

12. The method for simultaneously performing photodynamic therapy and photoacoustic measurement of claim 9, wherein emitting the pulsed light, further comprising:

emitting the pulsed light with a pulse repetition frequency of equal to or greater than 100 Hz and equal to or less than 10000 Hz.

13. The method for simultaneously performing photodynamic therapy and photoacoustic measurement of claim 9, wherein emitting the pulsed light, further comprising:

emitting the pulsed light with a pulse width of about 0.5 ms.

14. The method for simultaneously performing photodynamic therapy and photoacoustic measurement of claim 9, wherein emitting the pulsed light, further comprising:

emitting the pulsed light with a pulse power of about 225 mW.

* * * * *